US00PP11568P

United States Patent [19]

Zaiger et al.

[11] Patent Number: Plant 11,568

[45] Date of Patent: Oct. 17, 2000

[54] PEACH TREE NAMED 'SNOWFALL'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 09/211,793

[22] Filed: Dec. 15, 1998

[51] Int. Cl.[7] ..... A01H 5/00

[52] U.S. Cl. ..... Plt./196

[58] Field of Search ..... Plt./196

*Primary Examiner*—Howard J. Locker
*Assistant Examiner*—Melissa L. Kimball

[57] ABSTRACT

A new and distinct variety of peach tree (*Prunus persica*)the features of the tree and its fruit are characterized with the , tree budded on nemaguard rootstock, grown on Hanford sandy loam soil with Storie Index rating 95, in USDA Hardiness zone 9, near Modesto, Calif., and with standard commercial cultural fruit growing practices, such as, pruning, thinning, spraying, irrigation and fertilization. Its novelty consists of the following unique combination of features that are desirable in a new variety:

1. Heavy and regular production of fruit.
2. Fruit maturing in the late maturity season.
3. Large, firm, white flesh, freestone fruit.
4. Fruit with good storage and shipping quality.
5. Fruit that wll remain firm on the tree for approximately 2 weeks after maturity (shipping ripe).
6. Fruit having a sweet, sub-acid taste with very good flavor and eating quality.
7. Vigorous, upright growth.

1 Drawing Sheet

ORIGIN OF THE VARIETY

The present new and distinct variety of peach tree was originated by us in our experimental orchard located near Modesto, Calif., as a first generation cross between two selected seedlings with the field identification numbers 103ED581 and 258LC157. The maternal parent (103ED581) originated from a cross between O'Henry Peach (U.S. Plant Pat. No. 2,964) and a netarine of unknown parentage. The paternal parent (258LC157) originated from a cross between two selected seedlings with the field identification numbers 91ED457 and 108ED305. The selected seedling (91ED457) originated from a selected seedling of open pollinated O'Henry Peach seed crossed with a selected seedling of open pollinated May Grand Nectarine (U.S. Plant Pat. No. 2,794) seed. The select seedling (108Ed305) originated from a cross of White Lady Peach (U.S. Plant Pat. No. 5,821) crossed with a peach of unknown parentage. We planted a large group of these first generation seedlings on their own root and grew them under close and careful observation, during which time one such seedling, which represents the present variety, exhibited the desirable fruit characteristics described above and was selected for asexual reproduction and commercialization.

ASEXUAL REPRODUCTION OF THE VARIETY

Asexual reproduction of the new and distinct variety of peach tree was by budding to nemaguard rootstock, as performed by us in our experimental orchard located near Modesto, Calif., and shows that reproductions run true to the original tree and all characteristics of tree and the fruit are established and transmitted through succeeding asexual propagations.

SUMMARY OF THE VARIETY

The herein described variety of peach tree is of large size, vigorous, upright growth: and a regular, productive bearer of large, white flesh, freestone fruit with a mild, sweet, sub-acid taste with very good flavor and eating quality. The fruit is relatively large throughout the tree, holding firm on the tree approximately 2 weeks after maturity (shipping ripe). The firm flesh of the fruit exhibits good storage and shipping quality and the skin has an attractive red blush over the white ground color. The fruit ripens in the late maturity season, approximately 7 to 10 days after the late maturing peach variety September Snow (U.S. Plant Pat. No. 8,003).

PHOTOGRAPH OF THE VARIETY

The accompanying color photographic illustration shows typical specimens of the foliage and fruit of the present new peach variety. The illustration shows the upper and lower surface of the leaves, and exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Usually pruned 12 to 14 feet in height and 12 to 14 feet in width for economical harvesting of fruit.

*Vigor.*—Vigorous. Growth of 6 to 7 feet in first growing season, pruned 3 to 4 feet during first dormant season to select desirable primary scaffolds that will hold a heavy crop load.

*Form.*—Pruned to vase shape to allow for more sunlight to penetrate the center of tree to enhance the fruit color, increase Brix and keep fruit wood healthy.

*Productivity.*—Productive. Usually sets 2 or more times the desired amount and fruit must be thinned and spaced to the proper number for marketable size.

*Bearer.*—Regular. 5 years of consistent crops.

*Density.*—Medium dense. Leaves from a moderate amount of small branches and twigs prohibit sunlight from adequately penetrating the center of the tree for maximum fruit color.

*Growth.*—Upright. Normal growth is upright until heavy crop load spreads the tree.

*Hardiness.*—Tree grown in USDA Hardiness Zone 9. Winter chilling requirement estimated to be 800 to 1000 hours below 45° F.

Trunk:

*Size.*—Large.

*Texture.*—Medium shaggy.

*Color.*—Hair brown to soot brown (5-E-4) to (5-F-5).

Branches:

*Size.*—Medium.

*Texture.*—Smooth to medium rough, varies with age of growth.

*Lenticels.*—Medium number. Medium size.

*Color.*—Light brown to brown (5-D-7) to (5-E-7), varies with age of growth.

Leaves:

*Size.*—Large. Average length 7⅛ inches. Average width 1¾ inches.

*Form.*—Lanceolate, pointed.

*Margin.*—Crenate.

*Thickness.*—Medium.

*Surface.*—Smooth.

*Petiole.*—Medium length ½ inch. Medium thickness.

*Glands.*—Reniform. Number varies from 2 to 6. Average number 3. Medium size.

*Color.*—Upper surface — green to dark green (28-F-6) to (28-E-8). Lower surface — dull green to green (28-E-5) to (28-F-7).

Flower buds:

*Size.*—Medium to large.

*Length.*—Medium.

*Form.*—Plump.

*Pubescence.*—Pubescent.

Flowers:

*Size.*—Large — showy. Average diameter 1¼ inches.

*Pollen.*—Present — self fertile.

*Blooming period.*—Date of first bloom Feb. 25, 1997. Date of last bloom Mar. 3, 1997. Varies slightly with climatic conditions.

*Color.*—Pink to light pink (10-A-2) to (10-A-3). Color fades with age of bloom.

Fruit:

*Maturity when described.*—Firm ripe.

*Date of first picking.*—Sep. 5, 1997.

*Date of last picking.*—Sep. 12, 1997. Varies slightly with climatic conditions.

*Size.*—Large. Average diameter axially 3 to 3⅛ inches. Average transversely in suture plane 3 to 3 3/16 inches. Average weight 332.5 grams, varies from 310 to 350 grams.

*Form.*—Nearly globose, only slightly elongated in suture plane.

*Suture.*—Shallow, extends from base to apex.

*Ventral surface.*—Very slightly lipped, nearly rounded.

*Apex.*—Varies from rounded to slight pistil point.

*Base.*—Retuse.

*Cavity.*—Rounded to slightly elongated in suture plane. Average depth ⅝ inch. Average breadth 1 inch.

Flesh:

*Ripen.*—Evenly.

*Texture.*—Firm.

*Fibers.*—Few, small, tender.

*Aroma.*—Slight to moderate.

*Amygdalin.*—Undetected.

*Eating quality.*—Very good.

*Flavor.*—Very good.

*Soluble solids.*—Average 12.8° Brix, varies with number of fruit on tree, sunlight and temperature.

*Juice.*—Moderate — mild, sweet, enhances flavor.

*Color.*—White to very slight amount of pinkish white (9-A-1) to (9-A-2). Pit cavity — Bordeau red to garnet red (11-D-8) to (11-E-8). Red bleeding into flesh aroun pit cavity.

Stem:

*Size.*—Medium. Average length 9/32 inch. Average diameter 3/32 inch.

*Color.*—Light green to spring green (30-C-6) to (30-C-8).

Skin:

*Thickness.*—Medium.

*Texture.*—Medium — tenacious to flesh.

*Down.*—Moderate — medium length.

*Tendency to crack.*—None.

*Color.*—White to pinkish white ground color (9-A-1) to (9-A-2). Light red to red blush (11-A-4) to (11-C-8). Amount and degree of red blush varies with amount of skin exposure to the sunlight.

Stone:

*Type.*—Freestone.

*Size.*—Medium to large. Average length 1 7/16 inches. Average width 1 inch. Average thickness ¾ inch.

*Form.*—Obovate.

*Base.*—Usually straight, varies from straight to rounded.

*Apex.*—Cuspidate, medium size.

*Surface.*—Furrowed toward apex, pitted throughout, pits vary from round to slightly elongated. Ridges vary from sharp to rounded.

*Sides.*—Equal to unequal. Some stones with one side larger, extending farther from suture plane with slightly larger and deeper furrows and pits on outer surface.

*Tendency to split.*—None.

*Color.*—Brown to reddish brown (8-D-5) to (8-D-8).

Use:

*Market.*—Local and long distance.

Keeping quality:

*Good.*—Post harvest studies indicated 3 weeks in cold storage without internal breakdown of flesh.

Shipping quality:

*Good.*—Minimal bruising of flesh or skin scarring with packing and shipping trials.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth; and being a productive and regular bearer of large, firm, white flesh, freestone fruit with mild, sweet, sub-acid taste and very good flavor and eating quality; the fruit is further characterized by having firm flesh, good storage and shipping quality and ripening in the later maturity season, approximately 7 to 10 days later than the late maturing September Snow Peach (U.S. Plant Pat. No. 8,003).

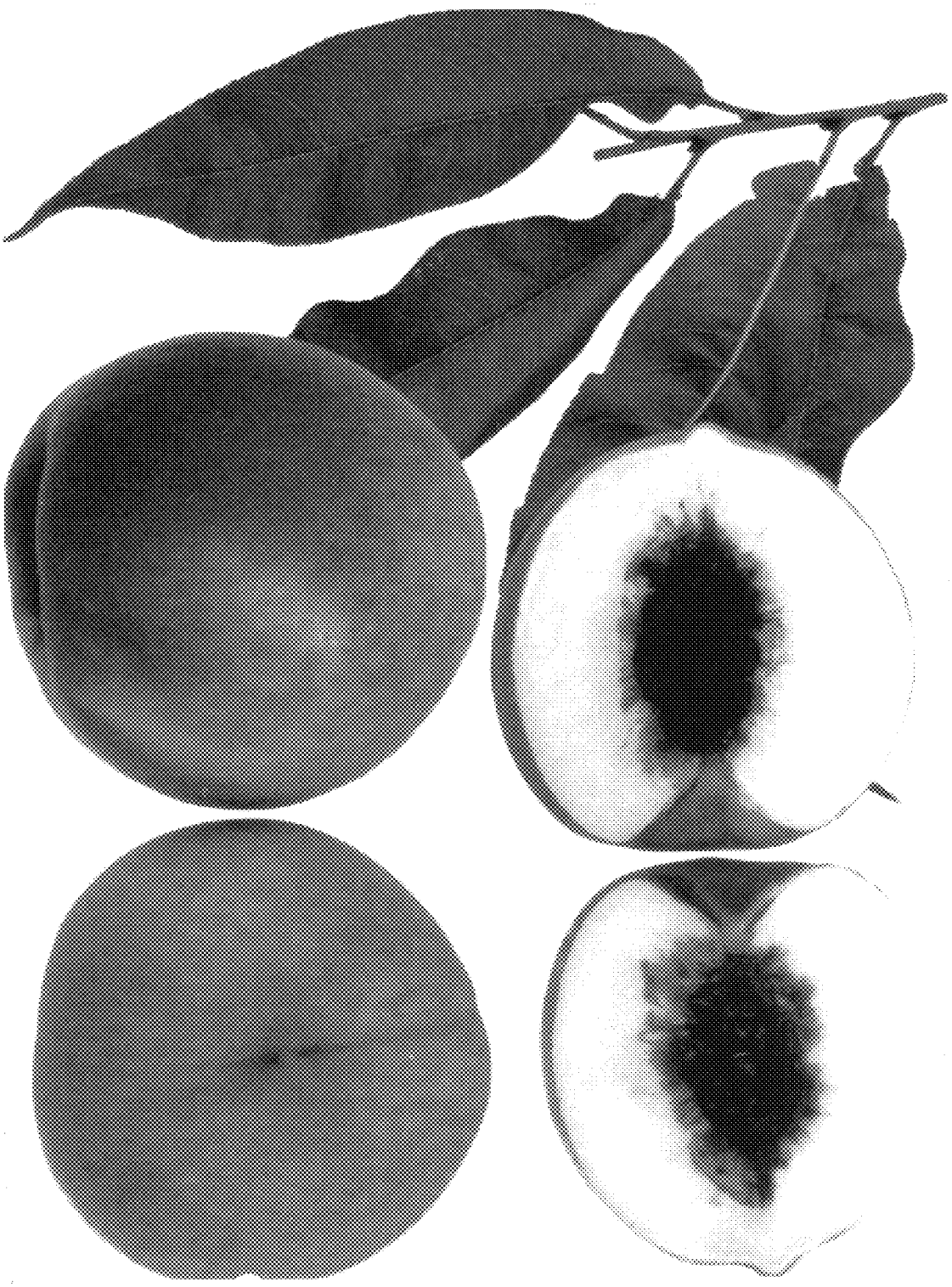

* * * * *